United States Patent [19]

Tahara et al.

[11] Patent Number: 4,892,872
[45] Date of Patent: Jan. 9, 1990

[54] BENZOXAZINE COMPOUNDS AND PHARMACEUTICAL USE THEREOF

[75] Inventors: Tetsuya Tahara; Takeshi Kawakita, both of Oita; Mitsuyoshi Yasumoto; Takemi Fukuda, both of Fukuoka, all of Japan

[73] Assignee: Yoshitomi Pharmaceutical Industries, Ltd., Osaka, Japan

[21] Appl. No.: 261,067

[22] Filed: Oct. 24, 1988

[30] Foreign Application Priority Data

Oct. 22, 1987 [JP] Japan .................................. 62-267953
Dec. 25, 1987 [JP] Japan .................................. 62-331259
Jan. 13, 1988 [JP] Japan ...................................... 63-5415

[51] Int. Cl.$^4$ .................... A61K 31/535; C07D 265/36
[52] U.S. Cl. .................................. 514/230.5; 544/105
[58] Field of Search ............................. 514/105, 230.5

[56] References Cited

FOREIGN PATENT DOCUMENTS 2509155 2/1975 Fed. Rep. of Germany .
3322574 11/1983 Fed. Rep. of Germany .
2153821 8/1985 United Kingdom .

OTHER PUBLICATIONS

The Lancet, Jun. 27, 1987, pp. 1470–1472.
Nature, vol. 316; Jul. 11, 1985, Richardson et al., pp. 126–131.

*Primary Examiner*—Richard L. Raymond
*Attorney, Agent, or Firm*—Sughrue, Mion, Zinn, Macpeak & Seas

[57] ABSTRACT

Benzoxazine compounds of the formula:

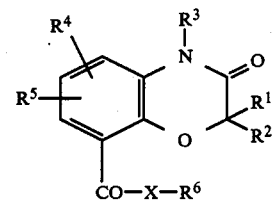

wherein each symbol is as defined in the specification. The compounds exhibit 5-HT$_3$ receptor antagonistic activity so that they are useful as antiemetics and so on.

5 Claims, No Drawings

BENZOXAZINE COMPOUNDS AND PHARMACEUTICAL USE THEREOF

BACKGROUND OF INVENTION

A new classification with respect to the serotonin (5-HT)-receptor subtype was suggested by B. P. Richardson et al as described in Nature, vol. 316, pp. 126 (1985), and the 5-HT M-receptor, which was proposed by Gaddum and Picarelli in 1957, was identified as a 5-HT$_3$ receptor.

It has been known that the 5-HT$_3$ receptor exists in the sensory nervous system, autonomic nervous terminal and so on, and it was also confirmed it was distributed in the central nervous system.

As the distribution of the 5-HT$_3$ receptor becomes clear, it is suggested that the clinical applicability of blocking agents against the 5-HT$_3$ receptor widely ranges from the peripheral system to the nervous system.

Metoclopramide is known to exhibit dopamine receptor antagonistic activity as well as 5-HT$_3$ receptor antagonistic activity and has been used in preventing vomiting or nausea induced by anticancer agents such as cisplatin, but its antiemetic effect is not satisfactory. Further, metoclopramide induces diarrhea and the adverse reaction in the central nervous system such as extrapyramidal disturbances or sedation.

According to various studies on the relationship of the 5-HT$_3$ receptor and vomiting, it is reported that a 5-HT$_3$ receptor antagonist is effective but a dopamine receptor antagonist is not effective against anticancer agent-induced vomiting.

The Lancet, June 27, 1987, pp, 1470 reports that the 5-HT$_3$ receptor antagonistic 8-methyl-8-azabicyclo[3.2.1]oct-3-yl indole-3-carboxylate (ICS 205-930) and 1,2,3,9-tetrahydro-9methyl-3-[(2-methyl-1H-imidazol-1-yl)methyl]-4H-carbazol-4-one hydrochloride (GR38032F) are effective against vomiting induced by chemotherapy, but show adverse effects such as headache, sedation, dryness of the mouth or diarrhea.

Therefore, it has been desired to develop 5-HT$_3$ receptor antagonistic antiemetics without side effects.

DE 2509155 A specification discloses a group of 1,4-benzoxazine compounds having antiarrhythmic activity.

The present inventors noticed that the 5-HT$_3$ receptor antagonists have various pharmacological activities such as antiemetic activity as well as potentiating activity of gastroenteromotility, analgesic activity and antiaxietic activity and made intensive investigations to develop a new and potent 5-HT$_3$ receptor antagonist without or with less and adverse effects; as a result, the inventors have found that a new series of benzoxazine compounds show an enhanced 5-HT$_3$ receptor antagonistic activity and completed the present invention.

SUMMARY OF THE INVENTION

The present invention provides potent 5-HT$_3$ receptor antagonistic benzoxazine compounds and pharmaceutical uses thereof.

DETAILED DESCRIPTION

The present invention relates to a benzoxazine compound of the formula:

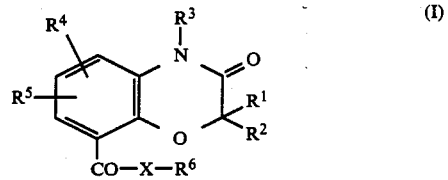

wherein $R^1$ and $R^2$ are the same or different, and each represents hydrogen or alkyl; $R^3$ represents hydrogen, alkyl, phenylalkyl or substituted phenylalkyl; $R^4$ and $R^5$ are the same or different, and each represents hydrogen, halogen, alkyl, alkoxy, amino, acylamino, alkylamino, hydroxy or nitro; X represents oxygen or NH; $R^6$ represents a group of the formula:

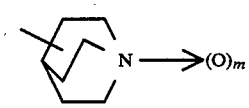

wherein m is 0 or 1, a group of the formula:

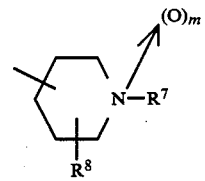

wherein $R^7$ represents alkyl, phenylalkyl, phenoxyalkyl, substituted phenylalkyl or substituted phenoxyalkyl, $R^8$ represents hydrogen or alkoxy and m is as defined above, or a group of the formula:

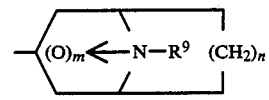

wherein $R^9$ represents alkyl, phenylalkyl or substituted phenylalkyl, n is 0 or 1, and m is as defined above, as well as an optical isomer thereof and a pharmaceutically acceptable salt thereof, and also to the pharmaceutical use thereof.

The definitions of the symbols in the formula (I) of the compounds of the present invention are hereinafter described in more detail. Halogen means fluorine, chlorine, bromine or iodine; alkyl means $C_{1-8}$ alkyl such as methyl, ethyl, propyl, isopropyl, butyl, isobutyl, t-butyl, pentyl, hexyl, heptyl or octyl; alkoxy means $C_{1-8}$ alkoxy such as methoxy, ethoxy, propoxy, isopropoxy, butoxy, isobutoxy, t-butoxy, pentyloxy, hexyloxy, heptyloxy or octyloxy; acylamino means $C_{2-5}$ alkanoylamino such as acetylamino, propionylamino, butyrylamino or pivaloylamino; alkylamino means that the alkyl moiety bears 1 to 8 carbon atoms and the amino moiety is substituted by mono- or di-alkyl, and includes methylamino, ethylamino, propylamino, isopropylamino, butylamino, hexylamino, octylamino, dimethylamino, diethylamino, dipropylamino, diisopropylamino, dibutylamino, dihexylamino or dioctylamino; phenylalkyl means that the alkyl moiety bears 1 to 4 carbon atoms, and includes benzyl, 2-phenylethyl, 1- phenylethyl, 3-phenylpropyl or 4-phenylbutyl; phenoxyalkyl having 1 to 4 carbon atoms in the alkyl moiety includes phenoxymethyl, 2-phenoxyethyl, 3-phenoxypropyl or 4-phenoxybutyl; the substituent(s) on the phenyl nucleus of phenylalkyl or phenoxyalkyl is(are) selected from the group consisting of 1 to 3 halogen atoms, alkoxy groups, alkyl groups, nitro groups, amino groups, trifluoromethyl groups, carboxy groups and alkoxycarbonyl groups, wherein the halogen, alkyl and alkoxy are as exemplified above.

The pharmaceutically acceptable salts of the compounds of formula (I) include acid addition salts such as hydrochloride, hydrobromide, phosphate, sulfate, p-toluenesufonate, citrate, lactate, maleate, fumarate or tartrate and, in the compounds having a carboxy group, salts with metal such as sodium, potassium, calcium, magnesium, zinc or aluminium, salts with an amine such as triethylamine and salts with an amino acid such as lysine or ornithine.

The preferable compounds of the present invention are the compounds of formula (I) wherein X represents NH and pharmaceutically acceptable salts thereof. More preferable compounds of the present invention are the compounds wherein $R^4$ represents chloro or bromo at the 6-position, X represents NH and $R^6$ represents quinuclidinyl and pharmaceutically acceptable salts thereof. Specific compounds of the present invention are selected from the group consisting of 6-chloro-3,4-dihydro-2-methyl-3-oxo-N-[3-quinuclidinyl)-2H-1,4-benzoxazine-8-carboxamide, 6-chloro-3,4-dihydro-2,4-dimethyl-3-oxo-N-(3-quinuclidinyl)-2H-benzoxazine-8-carboxamide, 6-chloro-3,4-dihydro-N-(8-methyl-8-azabicyclo[3.2.1]oct.-3-yl)-2,4-dimethyl-3-oxo-2-H-1,4-benzoxazine-8-carboxamide, 6-chloro-2-ethyl-3,4-dihydro-4-methyl-3-oxo-N-(3-quinuclidinyl)-2H-1,4-benzoxazine-8-carboxamide, 6-chloro-3,4-dihydro-4-methyl-3-oxo-N-(3-quinuclidinyl)-2H-1,4-benzoxazine-8-carboxamide, 6-bromo-3,4-dihydro-2,4-dimethyl-3-oxo-N-(3-quinuclidinyl)-2H-1,4-benzoxazine-8-carboxamide and 6-chloro-3,4-dihydro-2,2,4-trimethyl-3-oxo-N-(3-quinuclidinyl}-2H-1,4-benzoxazine-8-carboxamide, optical isomers thereof and pharmaceutically acceptable acid addition salts thereof (e.g. the hydrochloride).

The compounds of formula (I) of the present invention can be prepared by the following methods: (1) The compounds of formula (I) wherein m represents 0 can be prepared by reacting a compound of the formula:

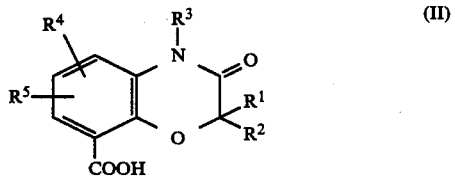

(II)

wherein each symbol is as defined above, or a functional derivative thereof with a compound of the formula:

$R^6a$—XH (III)

wherein $R^6a$ is as defined above except that m is 0 and X is as defined above.

(a) In case that the compounds of formula (II) are carboxylic acids, the reaction is usually carried out under cooling, at room temperature or under heating in an inert solvent in the presence of dicyclohexylcarbodiimide, titanium tetrachloride, phosphorus halide (e.g. phosphorus trichloride or phosphorus oxychloride), diethylchlorophosphite, o-phenylenechlorophosphite or ethyldichlorophosphite. The reaction can also be carried out by, in advance, reacting the compound of formula (III) with a phosphorus halide in an inert solvent, and then condensing with the compound of formula (II). When the phosphorus halide is phosphorus trihalide, the reaction is preferably carried out by previously reacting about ½ mole of phosphorus trihalide with the compound of formula (III) under cooling or at room temperature in the presence of a tertiary base such as triethylamine, pyridine or N,N-dimethylaniline, and then reacting the compound of formula (II) at room temperature or under warming, preferably under reflux with heating in an inert solvent.

(b) In the case that an acid halide such as an acid chloride or an acid bromide is used as a functional derivative of the carboxylic acid compounds of formula (II), the reaction is usually carried out under cooling or at room temperature in an inert solvent in the presence of a tertiary base such as triethylamine, pyridine or N,N-dimethylaniline, or under cooling or at room temperature in water in the presence of an alkali such as sodium hydroxide or potassium hydroxide.

(c) In the case that a symmetric acid anhydride or a mixed acid anhydride with, for example, an alkyl carbonate, an alkyl phosphate, an alkyl phosphite or sulfonic acid is used as a functional derivative of the carboxylic compounds of formula (II), the reaction is usually carried out under cooling, at room temperature or under warming in the presence of a tertiary amine such as triethylamine, pyridine or N,N-dimethylaniline in an inert solvent.

(d) When an active amide such as an acid imidazolide, an acid pyrrolidide or 2,4-dimethylpyrazolide is employed as a functional derivative of the compounds of formula (II), the reaction is usually carried out at room temperature or under warming in an inert solvent.

(e) The compounds of formula (III) wherein X represents NH can also be condensed with an ester compound such as methyl ester, ethyl ester, p-nitrophenyl ester or p-chlorophenyl ester as a functional derivative of the compounds of formula (II). The reaction is carried out at room temperature or under warming, preferably under reflux with heating in an inert solvent. The excess of compounds of formula (III) can also be used as the solvent.

The inert solvents which are usable in the above mentioned condensation reaction include, for example, benzene, toluene, xylene, methanol, ethanol, isopropyl alcohol, diethyl ether, dioxane, tetrahydrofuran, chloroform, dichloromethane, dichloroethane, hexamethylphosphoric triamide, diethylene glycol or dimethylformamide, or a mixed solvent thereof, and, when the compound of formula (II) is a functional derivative, it can be optionally selected in accordance with the type of the functional group.

The starting compounds of formula (II) can be, for example, prepared according to the following reaction scheme.

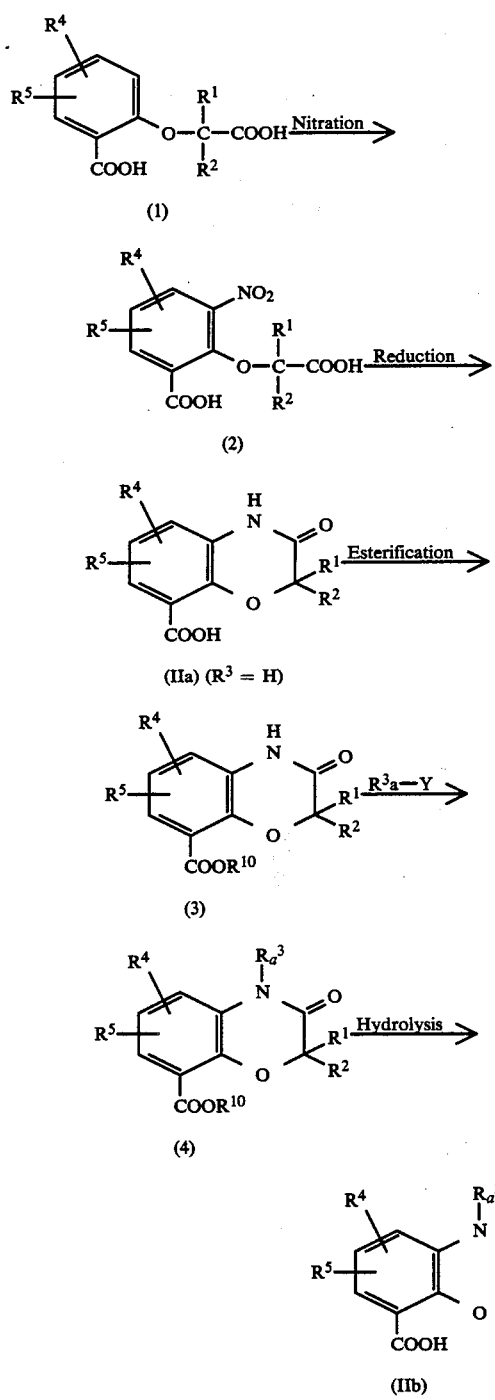

(IIa), reacting a compound of the formula: $R^3a$—Y with thus obtained compound (3) in the presence of an alkali metal compound such as potassium t-butoxide, and then hydrolyzing the thus obtained compound (4) with an alkali.

The intermediate compound (3) can also be prepared in accordance with the following reaction schemes:

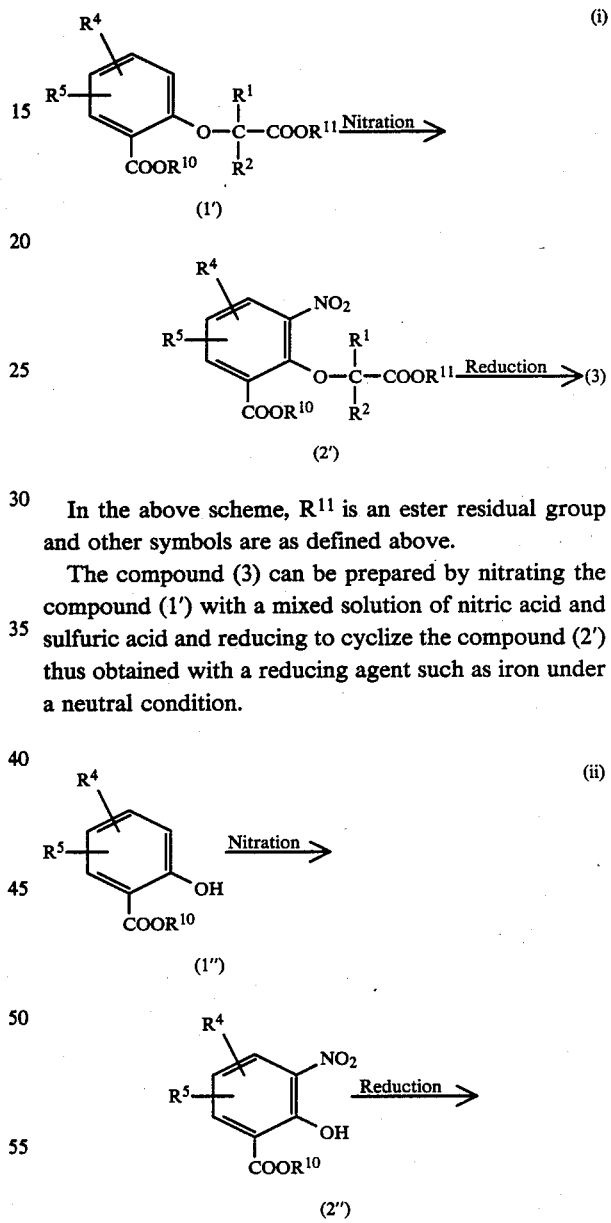

In the above scheme, $R^{11}$ is an ester residual group and other symbols are as defined above.

The compound (3) can be prepared by nitrating the compound (1') with a mixed solution of nitric acid and sulfuric acid and reducing to cyclize the compound (2') thus obtained with a reducing agent such as iron under a neutral condition.

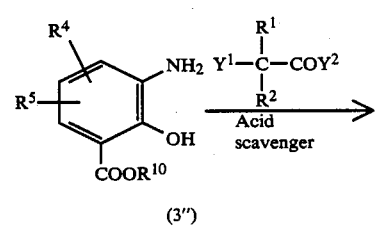

In the above scheme, $R^3a$ represents a group other than hydrogen in $R^3$, $R^{10}$ represents an ester residual group, Y represents a removable group such as chloro, bromo, iodo, methanesulfonyloxy or p-toluenesulfonyloxy and other symbols are as defined above.

The compounds of formula (IIa), i.e., the compounds of formula (II) wherein $R^3$ represents hydrogen, can be prepared by nitrating the compound (1) with a mixed solution of nitric acid and sulfuric acid, and reducing to cyclize the compound (2) obtained with a reducing agent such as ferrous sulfate, The compounds of formula (IIb) can be prepared by esterifying the compound

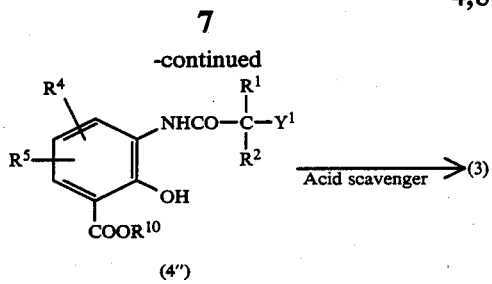

(4″)

In the above scheme, $Y^1$ and $Y^2$ are the same or different, and each represents a removable group such as halogen.

The compound (3) can be prepared by nitrating the compound (1″) with a mixed solution of nitric acid and sulfuric acid, reducing thus obtained compound (2″) with a reducing agent such as iron under a neutral condition, reacting compound (3″) thus obtained with compound (5) in the presence of an acid scavenger such as triethylamine or potassium carbonate, and then cyclizing the compound (4″) obtained with an acid scavenger.

Further, the compounds of formula (IIa) wherein $R^5$ represents nitro can be prepared by nitrating a compound of the formula (IIb) wherein $R^5$ represents hydrogen with a mixed solution of nitric acid and sulfuric acid. The compounds of formula (IIb) wherein $R^5$ represents amino can be prepared by reducing the thus obtained compound of formula (IIb) wherein $R^5$ represents nitro with a reducing agent such as iron or ferrous sulfate. Furthermore, the compounds of formula (IIb) wherein $R^5$ represents halogen can be prepared by diazonating the compounds of formula (IIb) wherein $R^5$ represents amino and then subjecting the product to Sandmeyer reaction with a cuprous halide such as cuprous chloride, cuprous bromide or cuprous iodide. The compounds of formula (IIb) wherein $R^5$ represents hydroxy can be prepared by diazonating the compounds of formula (IIb) wherein $R^5$ represents amino and treating with cuprous oxide-cupric nitrate according to the method of Cohen et al described in J. Org. chem., vol.42, pp.2053, 1977. The compounds of formula (IIb) wherein $R^5$ represents alkoxy can be prepared by reacting a compound of the formula (IIb) wherein $R^5$ represents hydroxy with an alkyl halide or dialkylsulfate in the presence of an acid scavenger. (2) The compounds of formula (I) wherein m represents 1 can be prepared by oxidizing the compounds of formula (I) wherein m represents 0 obtained in accordance with method (1).

The reaction is usually carried out at $-50°$ C. to room temperature, preferably at $-20°$ C. to $0°$ C., form 5 minutes to 24 hours, preferably for 5 minutes to 6 hours in an inert solvent such as chloroform, dichloromethane, tetrahydrofuran, dioxane, dimethylformamide, acetic acid or water, or a mixed solvent thereof. The oxidizing agent employed includes m-chloroperbenzoic acid, perbenzoic acid, peracetic acid, pertrifluoroacetic acid, permaleic acid, sodium bromite, sodium hypochlorite or hydrogen peroxide and can be used at a ratio of 1 to 10 equivalents, preferably 1 equivalent to a slightly excess amount. The oxidizing reaction is preferably carried out in the presence of a catalyst such as sodium tungstate.

While the compounds of formula (I) wherein $R^1$ and $R^2$ are different and/or the group of $R^6$—X—bears a chiral carbon atom can be obtained as a racemate, the individual optical isomers are embraced in the scope of the present invention. The racemic mixture can be optically divided in a conventional manner with an optically active acid such as tartaric acid, dibenzoyltartaric acid, mandelic acid or 10-camphorsulfonic acid, if desired. Further, the stereospecific compounds of formula (I) can be stereoselectively prepared by condensing an optically active carboxylic acid, obtained by optically dividing the racemate wherein $R^1$ and $R^3$ are different with an optically active base such as cinchonine, cinchonidine, brucine, quinine or α-methylbenzylamine, or a functional derivative thereof with an optically active compound of the formula (III), obtained by dividing with an optically active acid such as tartaric acid, dibenzoyltartaric acid, mandelic acid or 10-camphorsulfonic acid.

The compounds of formula (I) can be converted into a pharmaceutically acceptable acid addition salt such as hydrochloride, hydrobromide, phosphate, sulfate, p-toluenesulfonate, citrate, lactate, maleate, fumarate or tartrate. Moreover, the carboxylic compounds of formula (I) can be converted into a salt with a metal such as sodium, potassium, calcium, magnesium, zinc or aluminium, a salt with an amine such as triethylamine or a salt with an amino acid such as lysine or ornithine.

The following experiment will illustrate the 5-HT$_3$ receptor antagonistic action of the compounds (I) of the present invention.

Pharmacological experiment : Antagonistic effect against von Bezold-Jarish reflex 5-HT$_3$ receptor blocking effects of the compounds of the present invention were evaluated based on the antagonistic effects against von Bezold-Jarish reflex caused by administering serotonin to anesthetized rats as an index according to Forzard's method described in Naunyn-Schmiedeberg's Arch. Pharmacol., vol.326, pp.36, 1984.

Male Wistar rats weighing 350–450 g were anesthetized with an intraperitoneal injection of 1.25g/kg of urethane. The left jugular vein was cannulated for the intraveneous injection and the left femoral vein was cannulated for the measurement of blood pressure and heart rate. Serotonin (20 μg/kg) was intraveneously injected, and the compounds of the present invention were intraveneously injected 5 minutes before the challenge with serotonin. The antagonistic activity of the compounds of the present invention against the reflex bradycardia caused was measured and the mininum effective dose (MED, μg/kg) was determined. The results are summarized in Table 1.

TABLE 1

| Test Compound (Example No.) | MED (μg/kg, i.v.) |
|---|---|
| 5 | 0.5 |
| 14 | 0.5 |
| 15 | 0.5 |
| 17 | 0.5 |
| 29 | 0.5 |
| ICS 205-930 | 3.0 |
| GR 38032 F | 10.0 |

All ddy male mice survived by the oral administration (300 mg/kg) and the intraperitoneal injection (100 mg/kg) of the test compounds of the present invention for 5 days.

From the various pharmacological experiments including the above mentioned experiment, the compounds of the present invention exhibit so potent and selective a 5-HT$_3$ receptor antagonistic activity as well as patentiating activity of gastroenteromotility and antiemetic activity that they can be useful in preventing and/or treating various digestive system diseases such as dyspepsia, delayed extrusion of gastric contents or peptic ulcer; migraine; cluster headache; arrhythmia; vomiting caused by the administration of anticancer agents such as cisplatin; nausa or vomiting caused by actinotherapeutics; or disturbances in the central nervous system such as anxiety or psychosis.

The pharmaceutical composition for the prevention or treatment of the diseases as mentioned above comprises a therapeutically effective amount of the compounds of the present invention mixed with pharmaceutically acceptable additives such as a carrier, excepient or diluent. The pharmaceutical composition includes tablets, sugar-coated or film-coated tablets, granules, powder or an injectable solution and can be administered to the patients in need of such therapy without harmful adverse effects. The daily dose may vary depending upon the symptoms, body weights or ages of the patients, and preferably ranges about 0.1 to about 100 mg/kg by the oral administration for human adults in single or multiple dosage.

Pharmaceutical composition 1: Tablets

| Compound of Example 15 | 10.0 mg |
| --- | --- |
| Lactose | 30.0 mg |
| Corn starch | 19.8 mg |
| Crystalline cellulose | 28.0 mg |
| Talc | 2.0 mg |
| Magnesium stearate | 0.2 mg |
| Total | 90.0 mg |

A mixture of the compound of Example 15, lactose, corn starch and crystalline cellulose is kneaded with a part of the corn starch serving as a binder and granulated, and then dried at 50° C. for 3 hours. After the dried granules are passed through a 24-mesh sieve, talc and magnesium stearate are added thereto. Tablets weighing 90.0 mg each can be prepared by compressing the mixture with a punch of 6.0 mm diameter using a rotary compressor. Film-coated tablets can be prepared with 5 mg of a base for film coating comprising hydroxypropylmethyl cellulose and titanium oxide.

Pharmaceutical composition 2: Injectable solution

| Compound of Example 15 | 5.0 ml |
| --- | --- |
| Sodium chloride | 18.0 ml |
| Distilled water for injectable solution | q.s. 2.0 ml |

To a solution of sodium chloride in about 80 parts of distilled water for injection is dissolved the compound of Example 15. The 100 parts of solution is filtered through a membrane filter (0.2 μm), charged into a 2-ml volume ampule and then sterilized at 115° C. for 30 minutes.

The present invention will now be described in more detail by means of the following reference examples and working examples, but the invention is not limited thereto.

REFERENCE EXAMPLE 1.

To a solution of 220 g of 2-(2-carboxy-4-chlorophenoxy) propionic acid in 550 ml of concentrated sulfuric acid is added dropwise a mixed liquid of 44 ml of fuming nitric acid and concentrated sulfuric acid under stirring with keeping at a temperature below 10° C. After the addition, the reaction mixture is stirred below 10° C. for 3 hours and poured into 10 l of ice-cold water. The precipitated crystals are collected by filtration, washed with 2 l of water four times and them dried to give 190 g of 2-(2-carboxy-4-chloro-6-nitrophenoxy)propionic acid, melting at 190° C.

REFERENCE EXAMPLE 2

To a solution of 960 g of ferrous sulfate heptahydrate in 2 l of hot water is added a solution of 130 g of 2-(2-carboxy-4-chloro-6-nitrophenoxy)propionic acid and 200 ml of aqueous concentrated ammonia solution in 480 ml of water under stirring. After stirring for 30 minutes, to the reaction mixture is twice added 480 ml of aqueous concentrated ammonia solution. While the reaction mixture becomes exothermic, stirring is continued for an hour. The resultant mixture is filtered through a celite layer under reduced pressure and washed with 2 l of hot water twice. The filtrate is cooled and made acid with concentrated hydrochloric acid. The precipitated crystals are washed with water and dried to give 100 g of 6-chloro-3,4-dihydro-2-methyl-3-oxo-2H-1,4-benzoxazine-8-carboxylic acid, melting at 319°–320° C. with decomposition.

REFERENCE EXAMPLE 3

A mixture of 10 g of 6-chloro-3,4-dihydro-2-methyl-3-oxo-2H-1,4-benzoxazine-8-carboxylic acid, 150 ml of methanol and 5 ml of concentrated sulfuric acid is refluxed under heating with stirring for 40 hours, and then cooled. The precipitated crystals are collected by filtration, washed with methanol and dried to give 9.5 g of methyl 6-chloro-3,4-dihydro-2-methyl-3-oxo-2H-1,4-benzoxazine-8-carboxylate, melting at 186°–189° C.

REFERENCE EXAMPLE 4

To a solution of 4.85 g of methyl 6-chloro-3,4-dihydro-2-methyl-3-oxo-2H-1,4-benzoxazine-8-carboxylate in 30 ml of dimethylformamide is added 2.7 g of potassium t-butoxide and solution stirred at room temperature for 30 minutes. To the resultant solution is added dropwise a solution of 3.4 g of methyl iodide in 10 ml of dimethylformamide under stirring. After the reaction solution is stirred for 1.5 hours, 200 ml of water is added thereto. The insoluble substance is collected by filtration, washed with water and dried to give 5.1 g of methyl 6-chloro-3,4-dihydro-2,4-dimethyl-3-oxo-2H-1,4-benzoxazine-8-carboxylate, melting at 128°–130° C.

REFERENCE EXAMPLE 5

A mixture of 5.1 g of methyl 6-chloro-3,4-dihydro-2,4-dimethyl-3-oxo-2H-1,4-benzoxazine-8-carboxylate, 20 ml of ethanol and 50 ml of 4% aqueous potassium hydroxide solution is refluxed with heating for 5 hours. The resultant solution is cooled and 350 ml of water is added thereto followed by filtration. The filtrate is made acid with concentrated hydrochloric acid. The precipitated crystals are collected by filtration, washed with water and dried, and then recrystallized from ethanol to give 4.28 g of 6-chloro-3,4-dihydro-2,4-dimethyl-2H-1,4-benzoxazine-8-carboxylic acid, melting at 191°14 193° C.

REFERENCE EXAMPLE 6

A solution of 620 g of ethyl 4-chloro-2-methoxycarbonylphenoxyacetate in 1600 ml of concentrated sulfuric acid is cooled below 0° C, and a mixture of 102 ml of fuming nitric acid (d 1.50) and 102 ml of concentrated sulfuric acid is added dropwise below 5° C. The resultant solution is stirred for 3 hours under ice-cooling and poured into ice-cold water and then extracted with ethyl acetate. The extract is washed with water twice and dried over magnesium sulfate. The solvent is distilled off and the residue is gradually crystallized to give 697 g of ethyl 4-chloro-2-methoxycarbonyl-6-nitrophenoxyacetate, melting at 68°–70° C.

A solution of 100 ml of aqueous 0.78N ammonium chloride and 50 ml of dimethylformamide is heated at 85° C. and 40 g of powdery iron is added thereto under stirring followed by addition of a solution of 63.5 g of ethyl 4-chloro-2-methoxycarbonyl-6-nitrophenoxyacetate in 150 ml of dimethylformamide over 15 minutes. The reaction temperature rises to 95° C. The resulting solution is stirred at 80°–90° C. for an hour and 400 ml of dimethylformamide is added thereto. The whole solution is filtered with suction through hot celite. The mother liquor is poured into 2 l of ice-cold water and the precipitated crystals are collected by filtration to give 43.6 g of methyl 6-chloro-3,4-dihydro-3-oxo-2H-1,4-benzoxazine-8-carboxylate, melting at 239°–241° C.

REFERENCE EXAMPLE 7

To a solution of 100 g of methyl 5-chlorosalicylate and 250 ml of concentrated sulfuric acid (while keeping at a temperature below 0° C.) is added dropwise a mixture of 25 ml of fuming nitric acid (d 1.50) and 25 ml of concentrated sulfuric acid at a temperature below 5° C. The resultant solution is stirred under ice cooling for 0.5 hour and poured into ice-cold water. The precipitated crystals are collected by filtration and dried to give 122 g of methyl 5-chloro-3-nitrosalicylate, melting at 108°–110° C.

To 100 ml of an aqueous 0.78N ammonium chloride solution (with heating at 85° C.) is added 33.4 g of powdery iron with stirring followed by addition of a solution of 49.1 g of methyl 5-chloro-3-nitrosalicylate in 500 ml of toluene over 30 minutes. The reaction temperature rises to 95° C. The resultant solution is stirred at 80°–90° C. for an hour, and filtered with suction through hot celite. The mother liquor is poured into 1 l of ice-cold water, and the toluene layer is separated, washed with water and dried over magnesium sulfate. The solvent is distilled off and the residue is recrystallized from ethanol to give 25.4 g of methyl 3-amino-5-chlorosalicylate, melting at 65°–67° C.

To a solution of 8.9 g of methyl 3-amino-5-chlorosalicylate and 9.8 g of triethylamine in 200 ml of chloroform is added dropwise 21 g of 2-bromo-2-methylpropionyl bromide under ice-cooling and stirring, and then the solution stirred for 4 hours. The chloroform layer is separated, washed with water, diluted hydrochloric acid, aqueous sodium hydrogen carbonate and then water followed by drying over magnesium sulfate. The solvent is distilled off under reduced pressure and the residue is dissolved into methanol. To the solution is added an aqueous sodium carbonate solution and the solution stirred for an hour and then acidified with diluted hydrochloric acid followed by extracting with ethyl acetate. After the extract is washed with water and dried over magnesium sulfate, the solvent is distilled off under reduced pressure and the residue is recrystallized from isopropyl ether to give 10.2 g of methyl 3-(2-bromo-2-methylpropipnyl-amino)-5-chlorosalicylate, melting at 124°–125° C.

A mixture of 7.0 g of methyl 3-(2-bromo-2-methylpropionylamino)-5-chlorosalicylate, 3.6 g of potassium carbonate and 70 ml of dimethylformamide is stirred at 80° C. for 4 hours. After cooling, the resultant solution is poured into water and extracted with chloroform. The extract is washed with water and dried over magnesium sulfate followed by distillation of the solvent under reduced pressure to give 4.2 g of methyl 6-chloro-3,4-dihydro-2,2-dimethyl-3-oxo-2H-1,4-benzoxazine-8-carboxylate, melting at 178°–179° C.

To a solution of 4.2 g of methyl 6-chloro-3,4-dihydro-2,2-dimethyl-3-oxo-2H-1,4-benzoxazine-8-carboxylate in 20 ml of dimethylformamide is added 2.27 g of potassium t-butoxide, and the solution stirred at room temperature for 30 minutes. To the resultant solution is added dropwise a solution of 2.95 g of methyl iodide in 5 ml of dimethylformamide, and the solution stirred for 2.5 hours. To the resulting solution are added water and ethyl acetate to separate the organic layer followed by washing with water and drying over magnesium sulfate. After the solvent is distilled off under reduced pressure, to the residue are added 50 ml of ethanol and 50 ml of diluted aqueous sodium hydroxide solution and the system stirred at room temperature for 15 hours. To the resultant solution is added diluted hydrochloric acid and the precipitated crystals are collected by filtration and dried to give 3.9 g of 6-chloro-3,4-dihydro-2,2,4-trimethyl-3-oxo-2H-1,4-benzoxazine-8-carboxylic acid, melting at 235°–236° C.

REFERENCE EXAMPLE 8

To a solution of 60 g of 6-chloro-3,4-dihydro-4-methyl-3-oxo-2H-1,4-benzoxazine-8-carboxylic acid in 450 ml of concentrated sulfuric acid with cooling below 0° C. is added dropwise a mixture of 11.6 ml of fuming nitric acid and 11.6 ml of concentrated sulfuric acid at a temperature below 5° C. The resultant solution is stirred under ice-cooling for 2.5 hours and poured into ice-cold water. The precipitated crystals are collected by filtration and recrystallized from ethanol to give 6-chloro-3,4-dihydro-4-methyl-7-nitro-3-oxo-2H-1,4-benzoxazine-8-carboxylic acid, melting at 257° C. with decomposition.

REFERENCE EXAMPLE 9

To a solution of 85.5 g of 3,4-dihydro-4-methyl-3-oxo-2H-1,4-benzoxazine-8-carboxylic acid in 222 ml of concentrated sulfuric acid with cooling to −8° C. is added dropwise with stirring a mixture of 20.7 ml of fuming nitric acid (d 1.50) and 20.7 ml of concentrated sulfuric acid at a temperature below 2° C. over about 30 minutes, and the solution further stirred under cooling. The resultant solution is poured into ice-cold water with stirring. The precipitated crystals are collected by filtration, washed with water and dried to give 99 g of 3,4-dihydro-4-methyl-6-nitro-3-oxo-2H-1,4-benzoxazine-8-carboxylic acid, melting at 256°–259° C. with decomposition.

REFERENCE EXAMPLE 10

To 99 g of 3,4-dihydro-4-methyl-6-nitro-3-oxo-2H-1,4-benzoxazine-8-carboxylic acid is added portionwise 285 ml of thionyl chloride at room temperature, and the system heated with reflux for about an hour. After the resultant solution is dried under reduced pressure, to the residue is distilled off under reduced pressure. To the residue is added 200 ml of benzene to make the crystals finely particulate. After collecting by filtration, the crystals are washed with benzene and dried to give 103 g of 3,4-dihydro-4-methyl-6-nitro-3-oxo-2H-1,4-benzoxazine-8-carboxylic acid chloride.

In a similar manner as exemplified in the above reference examples, 6-chloro-3,4-dihydro-3-oxo-2H-1,4-benzoxazine-8-carboxylic acid (mp. 324° C.) 6-chloro-3,4-dihydro-4-methyl-3-oxo-2H-1,4-benzoxazine-8-carboxylic acid (mp. 241°-243° C.), 6-chloro-4-ethyl-3,4-dihydro-2-methyl-3-oxo-2H-1,4-benzoxazine-8-carboxylic acid, 6-chloro-2-ethyl-3,4-dihydro-4-methyl-3-oxo-2H-1,4-benzoxazine-8-carboxylic acid (mp. 196°-197° C.), 4-benzyl-6-chloro-3,4-dihydro-2-methyl-3-oxo-2H-1,4-benzoxazine-8-carboxylic acid [mp. 178°-179° C.), 6-bromo-3,4-dihydro-2,4-dimethyl-3-oxo-2H-1,4-benzoxazine-8-carboxylic acid (mp. 190°-192° C.), 6-chloro-3,4-dihydro-2-methyl-3-oxo-4-(2-phenylethyl)-2H-1,4-benzoxazine-8-carboxylic acid (mp.149° C.), 6-chloro-3,4-dihydro-2-methyl-4-(4-methylbenzyl)-3-oxo2H-1,4-benzoxazine-8-carboxylic acid (mp.194°-195° C.), 6-chloro-3,4-dihydro-2-methyl-3-oxo-4-(3-phenylpropyl)-2H -1,4-benzoxazine-8-carboxylic acid (mp. 126°-128° C.), 6-chloro-4-(4-fluorobenzyl)-3,4-dihydro-2-methyl-3-oxo-2H-1,4-benzoxazine-8-carboxylic acid (mp. 197°-198° C.}, 6-chloro-42,4-dichlorobenzyl)-3,4-dihydro-2-methyl-3-oxo-2H-1,4-benzoxazine-8-carboxylic acid (mp.202°-204° C.), 6-chloro-4-(3-trifluoromethylbenzyl -3,4-dihydro-2-methyl-3-oxo-2H-1,4-benzoxazine-8-carboxylic acid (mp. 144°-147° C.), 3,4-dihydro-4,6-dimethyl-3-oxo-2H-1,4-benzoxazine-8-carboxylic acid (mp. 192°-194° C.), 3,4-dihydro-6-methyl-3-oxo-2H-1,4-benzoxazine-8-carboxylic acid, 7-amino-6-chloro-3,4-dihydro-4-methyl-3-oxo-2H-1,4-benzoxazine-8-carboxylic acid (mp.250° C. with decomposition), 6,7-dichloro-3,4-dihydro-3-oxo-2H-1,4-benzoxazine-8-carboxylic acid, 6-bromo-3,4-dihydro-2-methyl 3-oxo-2H-1,4-benzoxazine-8-carboxylic acid (mp. 303°-305° C. with decomposition), 6-chloro-2-ethyl-3,4-dihydro-3-oxo-2H-1,4-benzoxazine-8-carboxylic acid (mp. 277°-279° C.), and 6-chloro-3,4-dihydro-4-(4-methoxybenzyl)-2-methyl-3-oxo-2H-1,4-benzoxazine-8-carboxylic acid (mp. 196°-197° C.) are obtained.

EXAMPLE 1

A solution of 4.6 g of 6-chloro-3,4-dihydro-3-oxo-2H-1,4-benzoxazine-8-carboxylic acid in 50 ml of tetrahydrofuran is cooled to below 0° C. and 5 ml of triethylamine is added under stirring thereto. Further, 2.5 g of ethyl chlorocarbonate is added and the mixture is stirred for an hour. To the resultant mixture is added 3.0 g of 3-aminoquinuclidine and the mixture stirred for 3 hours. After completion of the reaction, aqueous sodium hydrogen carbonate and ethyl acetate are added. The organic layer is separated, washed with water and dried over magnesium sulfate. The solvent is distilled off and the residue is recrystallized from ethanol-water followed by treating with ethanolic hydrochloric acid to give 6-chloro-3,4-dihydro-3-oxo-N-(3quinuclidinyl)-2H-1,4-benzoxazine-8-carboxamide hydrochloride, melting at 227°-229° C.

EXAMPLE 2

A solution of 4.8 g of 6-chloro-3,4-dihydro-2-methyl-3-oxo-2H-1,4-benzoxazine-8-carboxylic acid in 100 ml of tetrahydrofuran is cooled to below 0° C. and 5 ml of triethylamine is added under stirring thereto. Further, 2.5 g of ethyl chlorocarbonate is added and the mixture is stirred at room temperature for an hour. To the resultant mixture is added 3.0 g of 3-aminoquinuclidine and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is converted into the corresponding hydrochloride by treating with ethanolic hydrochloric acid followed by recrystallizing from ethanol-water to give 6-chloro-3,4-dihydro-2-methyl-3-oxo-N-(3-quinuclidinyl)-2H-1,4-benzoxazine-8-carboxamide hydrochloride, melting at 325°-328° C. with decomposition.

EXAMPLE 3

A solution of 4.8 g of 6-chloro-3,4-dihydro-2-methyl-3-oxo-2H-1,4-benzoxazine-8-carboxylic acid in 100 ml of tetrahydrofuran and 10 ml of dimethylformamide is cooled to below 0° C. and 5 ml of triethylamine is added under stirring thereto. Further, 2.5 g of ethyl chlorocarbonate is added and the mixture is stirred at room temperature for 45 minutes. To the resultant mixture is added 3.0 g of 3-amino-8-methyl-8-azabicyclo[3.2.1]octane and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is converted into the corresponding hydrochloride by treating with ethanolic hydrochloric acid followed by recrystallizing from ethanol-water to give 6-chloro-3,4-dihydro-2-methyl-N-(8-methyl-8-azabicyclo[3.2.1]oct-3-yl)-3-oxo-2H-1,4-benzoxazine-8-carboxamide hydrochloride, melting at 325°-328° C. with decomposition.

EXAMPLE 4

A solution of 4.2 g of 6-chloro-4-ethyl-3,4-dihydro-2-methyl-3-oxo-2H-1,4-benzoxazine-8-carboxylic acid in 100 ml of tetrahydrofuran is cooled to below 0° C. and 5 ml of triethylamine is added under stirring thereto. Further, 2.0 g of ethyl chlorocarbonate is added and the mixture is stirred for 30 minutes. To the resultant mixture is added 3.0 g of 3-aminoquinuclidine and the mixture stirred for 5 hours. After completion of the reaction, aqueous sodium hydrogen carbonate and ethyl acetate are added. The organic layer is separated, washed with water and dried over magnesium sulfate. The solvent is distilled off and the residue is converted into the corresponding hydrochloride by treating with ethanolic hydrochloric acid followed by recrystallizing from ethanol-ethyl acetate to give 6-chloro-4-ethyl-3,4-dihydro-2-methyl-3-oxo-N-(3-quinuclidinyl)-2H-1,4-benzoxazine-8-carboxamide hydrochloride, melting at 249°-252° C.

EXAMPLE 5

A solution of 4.28 g of 6-chloro-3,4-dihydro-2,4-dimethyl-3-oxo-2H-1,4-benzoxazine-8-carboxylic acid in 50 ml of tetrahydrofuran is cooled to below 0° C. and 5 ml of triethylamine is added under stirring thereto. Further, 2.0 g of ethyl chlorocarbonate is added and the mixture is stirred for 30 minutes. To the resultant mixture is added 3.0 g of 3-aminoquinuclidine and the mixture stirred for 5 hours. After completion of the reaction, aqueous sodium hydrogen carbonate and ethyl acetate are added. The organic layer is separated, washed with water and dried over magnesium sulfate. The solvent is distilled off and the residue is converted into the corresponding hydrochloride by treating with ethanolic hydrochloric acid followed by recrystallizing from ethanolethyl acetate to give 6-chloro-3,4-dihydro-2,4-dimethyl-3-oxo-N-(3-quinuclidinyl)-2H-1,4-benzoxazine-8-carboxamide hydrochloride, melting at 286°–289° C.

EXAMPLE 6

A solution of 4.56 g of 6-chloro-3,4-dihydro-3-oxo-2H-1,4-benzoxazine-8-carboxylic acid in 100 ml of tetrahydrofuran and 10 ml of dimethylformamide is cooled to below 0° C. and 2.2 ml of triethylamine is added under stirring thereto. Further, 2.3 g of ethyl chlorocarbonate is added and the mixture is stirred at a temperature below 5° C. for an hour. To the resultant mixture is added 4.2 g of 4-amino-1-(2-phenylethyl)piperidine and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is recrystallized from ethyl acetate-ethanol to give 6-chloro-3,4-dihydro-3-oxo-N-[1-(2-phenylethyl)-4-piperidyl]-2H-1,4-benzoxazine-8-carboxamide, melting at 233°–235° C.

EXAMPLE 7

A solution of 2.3 g of 6-chloro-3,4-dihydro-3-oxo-2H-1,4-benzoxazine-8-carboxylic acid in 100 ml of tetrahydrofuran is cooled to below 0° C. and 2 ml of triethylamine is added under stirring thereto. Further, 1.1 g of ethyl chlorocarbonate is added and the mixture is stirred for 3 hours. To the resultant mixture is added 2.5 g of 4-amino-1-(3-phenoxypropyl)piperidine and the mixture stirred for 8 hours followed by collecting by filtration and washing with tetrahydrofuran and water. To a suspension of thus obtained crystals in 100 ml of methanol are added 10 ml of 10% hydrochloric acid and 30 ml of water and then the suspension is stirred. The collection of the crystals by filtration gives 6-chloro-3,4-dihydro-3-oxo-N-[1-(3-phenoxypropyl)-4-piperidyl]-2H-1,4 -benzoxazine-8-carboxamide hydrochloride, melting at 290°–300° C. with decomposition.

EXAMPLE 8

A solution of 4.5 g of 6-chloro-3,4-dihydro-3-oxo-2H-1,4-benzoxazine-8-carboxylic acid in 100 ml of tetrahydrofuran and 10 ml of dimethylformamide is cooled to below 0° C. and 2.5 ml of triethylamine is added under stirring thereto. Further, 2.4 g of ethyl chlorocarbonate is added and the mixture is stirred while keeping below 50° C. for an hour. To the resultant mixture is added 3.6 g of 3-amino-1benzylpiperidine and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is recrystallized from ethanol-ethyl acetate to give N-(1-benzyl-4-piperidyl) -6-chloro-3,4-dihydro-3-oxo-2H-1,4-benzoxazine-8-carboxamide, melting at 203°–206° C.

EXAMPLE 9

A solution of 4.18 g of 6-chloro-3,4-dihydro-2,4-dimethyl-3-oxo-2H-1,4-benzoxazine-8-carboxylic acid in 50 ml of tetrahydrofuran is cooled to below 0° C. and 1.6 ml of triethylamine is added under stirring thereto. Further, 2.2 g of isobutyl chlorocarbonate is added and the mixture is stirred at room temperature for 45 minutes. To the resultant mixture is added 2.25 g of 3-amino-8-methyl-8-azabicyclo[ [3.2.1]octane and the mixture stirred for 4 hours. After completion of the reaction, aqueous sodium hydrogen carbonate and ethyl acetate are added. The organic layer is separated, washed with water and dried over magnesium sulfate. The solvent is distilled off and purified by chromatography on silica gel using a 50:1 mixture of chloroform and methanol as an eluent. The corresponding hydrochloride obtained by treating with ethanolic hydrochloric acid is recrystallized from ethanol to give 6-chloro-3,4-dihydro-(8-methyl-8-azabicyclo[3.2.1]oct-3-yl) -2,4-dimethyl-2H-1,4-benzoxazine-8-carboxamide hydrochloride, melting at 273° C. with decomposition.

EXAMPLE 10

A solution of 4.0 g of 6-chloro-3,4-dihydro-2,4-dimethyl-3-oxo-2H-1,4-benzoxazine-8-carboxylic acid in 80 ml of tetrahydrofuran is cooled to below 0° C. and 3.17 g of N-methylmorpholine is added under stirring thereto. Further, 2.35 g of isobutyl chlorocarbonate is added and the mixture is stirred at the same temperature for an hour. To the resultant mixture is added 3.28 g of 3-amino-1-benzylpiperidine and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is recrystallized from ethanol followed by treating with ethanolic hydrochloric acid to give N-(1-benzyl-4-piperidyl)-6-chloro-3,4-dihydro-2,4-dimethyl- 3-oxo-2H-1,4-benzoxazine-8-carboxamide hydrochloride, melting at 214° C. with decomposition.

EXAMPLE 11

A solution of 4.0 g of 6-chloro-3,4-dihydro-2,4-dimethyl-3-oxo-2H-1,4-benzoxazine-8-carboxylic acid in 80 ml of tetrahydrofuran is cooled to below 0° C. and 3.17 g of N-methylmorpholine is added under stirring thereto. Further, 2.35 g of isobutyl chlorocarbonate is added and the mixture is stirred at the same temperature for 45 minutes. To the resultant mixture is added 3.52 g of 4-amino-1-(2-phenylethyl)piperidine and the mixture stirred for 2 hours. After completion of the reaction, aqueous sodium hydrogen carbonate and ethyl acetate are added. The organic layer is separated, and diluted hydrochloric acid is added thereto. The precipitated crystals are collected by filtration and recrystallized from ethanol to give 6-chloro-3,4-dihydro-2,4-dimethyl-3-oxo-N-[1-(2-phenylethyl)-4-piperidyl]-2H-1,4-benzoxazine-8-carboxamide hydrochloride monohydrate, melting at 257°–259° C. with decomposition.

EXAMPLE 12

A solution of 4.0 g of 6-chloro-3,4-dihydro-2,3-dimethyl-3-oxo-2H-1,4-benzoxazine-8-carboxylic acid in 80 ml of tetrahydrofuran is cooled to below 0° C. and 3.17 g of N-methylmorpholine is added under stirring thereto. Further, 2.35 g of isobutyl chlorocarbonate is added and the mixture is stirred at the same temperature for 45 minutes. To the resultant mixture is added 3.28 g of 3-amino-1-benzylpiperidine and the mixture stirred for 4 hours. After completion of the reaction, aqueous sodium hydrogen carbonate and ethyl acetate are added. The organic layer is separated, washed with water and dried over magnesium sulfate. The solvent is distilled off and the residue is recrystallized from ethanol followed by treating with ethanolic hydrochloric acid to give N-(1-benzyl-3-piperidyl)-6-chloro-3,4-dihydro-2,4-dimethyl3-oxo-2H-1,4-benzoxazine-8-carboxamide hydrochloride hemihydrate, melting at 174°–176° C. with decomposition.

EXAMPLE 13

A solution of 4.0 g of 6-chloro-3,4-dihydro-2,4-dimethyl-3-oxo-2H-1,4-benzoxazine-8-carboxylic acid in 80 ml of tetrahydrofuran is cooled to below 0° C. and 3.17 g of N-methylmorpholine is added under stirring thereto. Further, 2.35 g of isobutyl chlorocarbonate is added and the mixture is stirred at the same temperature for 45 minutes. To the resultant mixture is added 3.77 g of 3-amino-1-(3-phenylpropyl)piperidine and the mixture stirred for 3 hours. After completion of the reaction, aqueous sodium hydrogen carbonate and ethyl acetate are added. The organic layer is separated, washed with water and dried over magnesium sulfate. The solvent is distilled off and the residue is recrystallized from ethanol followed by treating with ethnnolic hydrochloric acid to give 6-chloro-3,4-dihydro-2,4-dimethyl-3-oxo-N-[1-( 3-phenylpropyl)-4-piperidyl]-2H-1,4-benzoxazine-8carboxamide hydrochloride, melting at 174°–176° C. with decomposition.

EXAMPLE 14

To a solution of 2.43 g of 3-aminoquinuclidine and 2.5 g of N-methylmorpholine in 50 ml of chloroform is added 5.2 g of 6-chloro-2-ethyl-3,4-dihydro-4-methyl-3-oxo-2H-1,4-benzoxazine-8-carboxylic acid chloride under cooling and stirring followed by stirring for 2 hours. The resultant solution is washed with water, aqueous sodium hydrogen carbonate and then water, and dried over magnesium sulfate. After the solvent is distilled off under reduced pressure, the residue is recrystallized from ethanolisopropyl ether and treated with ethanolic hydrochloric acid to give 6-chloro-2-ethyl-3,4-dihydro-4-methyl-3-oxo-N-(3-quinuclidinyl)-2H-1,4-benzoxazine-8-carboxamide hydrochloride, melting at 295° C. with decomposition.

EXAMPLE 15

To a solution of 3.0 g of 3-aminoquinuclidine and 3.0 g of N-methylmorpholine in 60 ml of chloroform is added 6.2 g of 6-chloro-3,4-dihydro-4-methyl-3-oxo-2H-1,4-benzoxazine-8-carboxylic acid chloride under cooling and stirring followed by stirring for 2 hours. The resultant solution is washed with water, aqueous sodium hydrogen carbonate and then water, and dried over magnesium sulfate. After the solvent is distilled off under reduced pressure, the residue is recrystallized from ethanol-isopropyl ether and treated with ethanolic hydrochloric acid to give 6-chloro-3,4-dihydro-4-methyl-3-oxo-N-(3-quinuclidinyl)-2H-1,4-benzoxazine-8-carboxamide hydrochloride, melting at 281° C. with decomposition.

EXAMPLE 16

To a solution of 1.09 g of 3-aminoquinuclidine and 0.9 g of N-methylmorpholine in 20 ml of chloroform is added a solution of 3.25 g of 4-benzyl-6-chloro-2-ethyl-3,4-dihydro -2-methyl-3-oxo-2H-1,4-benzoxazine-8-carboxylic acid chloride in 20 ml of chloroform under cooling and stirring followed by stirring at room temperature for 4 hours. The resultant solution is washed with water, aqueous sodium hydrogen carbonate and then water, and dried over magnesium sulfate. After the solvent is distilled off under reduced pressure, the residue is recrystallized from ethanolisopropyl ether and treated with ethanolic hydrochloric acid to give 4-benzyl-6-chloro-3,4-dihydro-2-methyl-3-oxo-N-(3-quinuclidinyl)-2H-1,4-benzoxazine-8-carboxamide hydrochloride, melting at 267°–270° C. with decomposition.

EXAMPLE 17

To a solution of 1.6 g of 3-aminoquinuclidine and 1.35 g of N-methylmorpholine in 25 ml of chloroform is added a solution of 4.0 g of 6-bromo-3,4-dihydro-2,4-dimethyl-3-oxo -2H-1,4-benzoxazine-8-carboxylic acid chloride in 20 ml of chloroform under cooling and stirring followed by stirring at room temperature for 3 hours. The resultant solution is washed with water, aqueous sodium hydrogen carbonate and then water, and dried over magnesium sulfate. After the solvent is distilled off under reduced pressure, the residue is recrystallized from ethanol-isopropyl ether to give 6-bromo-3,4-dihydro-2,4-dimethyl-3-oxo-N-(3-quinuclidinyl) -2H-1,4-benzoxazine-8-carboxamide, melting at 287°–288° C.

EXAMPLE 18

To a solution of 1.2 g of 3-aminoquinuclidine and 1.2 g triethylamine in 50 ml of chloroform is added a solution of 3.45 g of 6-chloro-3,4-dihydro-2-methyl-3-oxo-4-(2phenylethyl) -2H-1,4-benzoxazine-8-carboxylic acid chloride in 20 ml of chloroform under cooling and stirring followed by stirring at room temperature for 4 hours. The resultant solution is washed with water, aqueous sodium hydrogen carbonate and then water, and dried over magnesium sulfate. After the solvent is distilled off under reduced pressure, the residue is recrystallized from ethanolisopropyl ether and treated with ethanolic hydrochloric acid to give 6-chloro-3,4-dihydro-2-methyl-3-oxo-4-(2-phenylethyl)-N-(3-quinuclidinyl)-2H-1,4-benzoxazine-8-carboxamide hydrochloride hemihydrate, melting at 207° C. with decomposition.

EXAMPLE 19

To a solution of 1.2 g of 4-amino-1-[3-(4-fluorophenoxy)propyl]-3-methoxypiperidine and 1.2 g of triethylamine in 50 ml of chloroform is added a solution of 2.5 g of 6-chloro-3,4-dihydro-4-methyl-3-oxo-2H-1,4-benzoxazine-8-carboxylic acid chloride in 10 ml of chloroform under cooling and stirring followed by stirring at room temperature for 4 hours. The resultant solution is washed with water, aqueous sodium hydrogen carbonate and then water, and dried over magnesium sulfate. After the solvent is distilled off under reduced pressure, the residue is purified by chromatography on silica gel using chloroform as an eluent, recrystallized from ethanol and treated with ethanolic hydrochloric acid to give 6-chloro-N-{1-[3-(4-fluorophenoxy)-propyl]-3-methoxy-4-piperidyl}-3,4-dihydro-4-methyl-3-oxo-2H-1,4-benzoxazine-8-carboxamide hydrochloride hemihydrate, melting at 230° C. with decomposition.

EXAMPLE 20

To a solution of 1.66 g of 3-aminoquinuclidine and 1.4 g of N-methylmorpholine in 30 ml of chloroform is added a solution of 5.0 g of 6-chloro-3,4-dihydro-4-(4-methoxybenzyl)-2-methyl-3-oxo-2H-1,4-benzoxazine-8-carboxylic acid chloride in 20 ml of chloroform under cooling and stirring followed by stirring for 2 hours.

The resultant solution is washed with water, aqueous sodium hydrogen carbonate and then water, and dried over magnesium sulfate. After the solvent is distilled off under reduced pressure, the residue is recrystallized from ethanol-isopropyl ether and treated with fumaric acid, and then recrystallized from methanol-isopropyl ether to give 6-chloro-3,4-dihydro-4-(4-methoxybenzyl)-2 -methyl-3-oxo-N-(3-quinuclidinyl)-2H-1,4-benzoxazine-8-carboxamide fumarate, melting at 205° C. with decomposition.

EXAMPLE 21

To a solution of 1.39 g of 3-aminoquinuclidine and 1.2 g of N-methylmorpholine in 30 ml of chloroform is added a solution of 4.2 g of 6-chloro-3,4-dihydro-2-methyl-4-(4-methylbenzyl)-3-oxo-2H-1,4-benzoxazine-8-carboxylic acid chloride is 25 ml of chloroform under cooling and stirring followed by stirring for 2 hours. The resultant solution is washed with water, aqueous sodium hydrogen carbonate and then water, and dried over magnesium sulfate. After the solvent is distilled off under reduced pressure, the residue is recrystallized from ethanol-isopropyl ether and treated with fumaric acid and then recrystallized from ethanol to give 6-chloro-3,4-dihydro-2-methyl-4-(4-methylbenzyl)-3-oxo-N-(3-quinuclidinyl)-2H-1,4-benzoxazine-8-carboxamide hemifumarate, melting at 156° C. with decomposition.

EXAMPLE 22

To a solution of 1.50 g of 3-aminoquinuclidine and 1.3 g of N-methylmorpholine in 30 ml of chloroform is added a solution of 4.5 g of 6-chloro-3,4-dihydro-2-methyl-3-oxo-4-(3-phenylpropyl)-2H-1,4-benzoxazine-8-carboxylic acid chloride in 20 ml of chloroform under cooling and stirring followed by stirring for 4 hours. The resultant solution is washed with water, aqueous sodium hydrogen carbonate and then water, and dried over magnesium sulfate. After the solvent is distilled off under reduced pressure, the residue is purified with column chromatography using chloroform as an eluent and treated with ethanolic hydrochloric acid to give 6-chloro-3,4-dihydro-2-methyl-3-oxo-4-(3-phenylpropyl)-N-(3-quinuclidinyl)-2H-1,4-benzoxazine-8-carboxamide hydrochloride hemihydrate, melting at 274°-277° C. with decomposition.

EXAMPLE 23

To a solution of 1.80 g of 3-aminoquinuclidine and 1.5 g of N-methylmorpholine in 3 ml of chloroform is added a solution of 5.0 g of 6-chloro-4-(4-fluorobenzyl)-3,4-dihydro-2-methyl-3-oxo-2H-1,4-benzoxazine-8-carboxylic acid chloride in 20 ml of chloroform under cooling and stirring followed by stirring for 4 hours. The resultant solution is washed with water, aqueous sodium hydrogen carbonate and then water, and dried over magnesium sulfate. After the solvent is distilled off under reduced pressure, the residue is purified with column chromatography using chloroform as an eluent and treated with ethanolic hydrochloric acid to give 6-chloro-4-(4-fluorobenzyl)-3,4-dihydro-2-methyl-3-oxo-N-(3-quinuclidinyl)-2H-1,4-benzoxazine-8-carboxamide hydrochloride monohydrate, melting at 117°-119° C. with decomposition.

EXAMPLE 24

To a solution of 1.14 g of 3-aminoquinuclidine and 1.0 g of N-methylmorpholine in 30 ml of chloroform is added a solution of 3.8 g of 6-chloro-4-(2,4-dichlorobenzyl)-3,4-dihydro-2-methyl-3-oxo-2H-1,4-benzoxazine-8-carboxylic acid chloride in 20 ml of chloroform under cooling and stirring followed by stirring for 4 hours. The resultant solution is washed with water, aqueous sodium hydrogen carbonate and then water, and dried over magnesium sulfate. After the solvent is distilled off under reduced pressure, the residue is purified with column chromatography using chloroform as an eluent and treated with ethanolic hydrochloric acid to give 6-chloro-4-(2,4-dichlorobenzyl)-3,4-dihydro-2-methyl-3-oxo-N-(3-quinuclidinyl)-2H-1,4-benzoxazine-8-carboxamide hydrochloride monohydrate, melting at 170°-173° C. with decomposition.

EXAMPLE 25

To a solution of 1.35 g of 3-aminoquinuclidine and 1.14 g of N-methylmorpholine in 30 ml of chloroform is added a solution of 4.5 g of 6-chloro-4-(3-trifluoromethylbenzyl)-3,4-dihydro-2-methyl-3-oxo-2H-1,4-benzoxazine-8-carboxylic acid chloride in 20 ml of chloroform under cooling and stirring followed by stirring for 4 hours. The resultant solution is washed with water, aqueous sodium hydrogen carbonate and then water, and dried over magnesium sulfate. After the solvent is distilled off under reduced pressure, the residue is recrystallized from ethanol and treated with ethanolic hydrochloric acid to give 6-chloro-4-(3-trifluoromethylbenzyl)-3,4-dihydro-2-methyl-3-oxo-N-(3-quinuclidinyl)-2H-1,4-benzoxazine-8-carboxamide hydrochloride, melting at 271°-274° C. with decomposition.

EXAMPLE 26

To a solution of 2.56 g of 3-aminoquinuclidine and 2.16 g of N-methylmorpholine in 40 ml of chloroform is added a solution of 4.72 g of 3,4-dihydro-4,6-dimethyl-3-oxo-2H-1,4-benzoxazine-8-carboxylic acid chloride in 20 ml of chloroform under cooling and stirring followed by stirring for 3 hours. The resultant solution is washed with water, aqueous sodium hydrogen carbonate and then water, and dried over magnesium sulfate. After the solvent is distilled off under reduced pressure, the residue is purified with column chromatography using chloroform as an eluent and treated with ethanolic hydrochloric acid to give 3,4-dihydro-4,6-dimethyl-3-oxo-N-(3-quinuclidinyl)-2H-1,4-benzoxazine-8-carboxamide hydrochloride, melting at 283°-284° C. with decomposition.

EXAMPLE 27

To a solution of 2.91 g of 3-aminoquinuclidine and 2.46 g of N-methylmorpholine in 30 ml of chloroform is added a solution of 5.0 g of 3,4-dihydro-4-methyl-3-oxo-2H-1,4-benzoxazine-8-carboxylic acid chloride in 70 ml of chloroform under cooling and stirring followed by stirring for 7 hours. The resultant solution is washed with water, aqueous sodium hydrogen carbonate and then water, and dried over magnesium sulfate. After the solvent is distilled off under reduced pressure, the residue is purified with column chromatography using chloroform as an eluent and treated with ethanolic hydrochloric acid to give 3,4-dihydro-4-methyl-3-oxo-N-(3 -quinuclidinyl)-2H-1,4-benzoxazine-8-carboxamide hydrochloride, melting at 271°-272° C. with decomposition.

EXAMPLE 28

To a solution of 2.39 g of 3-quinuclidinol and 2.1 g of N-methylmorpholine in 30 ml of chloroform is added 5.8 g of 6-chloro-3,4-dihydro-4-methyl-3-oxo-2H-1,4-benzoxazine-8-carboxylic acid chloride under cooling and stirring followed by stirring for 3 hours. The resultant solution is washed with water, and dried over magnesium sulfate. After the solvent is distilled off under reduced pressure, the residue is purified with column chromatography using chloroform as an eluent and treated with ethanolic hydrochloric acid to give quinuclidinyl 6-chloro-3,4-dihydro-4-methyl-3-oxo-N-(3-quinuclidinyl)-2H-1,4-benzoxazine-8-carboxylate hydrochloride, melting at 295° C. with decomposition.

EXAMPLE 29

A mixture of 3.5 g of 6-chloro-3,4-dihydro-2,2,4-trimethyl-3-oxo-2H-1,4-benzoxazine-8-carboxylic acid and 5 ml of thionyl chloride is refluxed under heating for 1.5 hours. After completion of the reaction, the excess thionyl chloride is distilled off under reduced pressure, and further 50 ml of benzene is added thereto followed by complete removal of thionyl chloride by distillation under reduced pressure. A solution of the residue in 50 ml of chloroform is added dropwise to a solution of 2.6 g of 3-aminoquinuclidine dihydrochloride and 4.7 g of triethylamine under cooling and stirring. The resultant solution is stirred at room temperature for 2 hours, and then washed with water and dried over magnesium sulfate. After the solvent is distilled off under reduced pressure, the residue is recrystallized from ethanol-isopropyl ether followed by treating with ethanolic acid to give 6-chloro-3,4-dihydro-2,2,4-trimethyl-3-oxo-N-(3-quinuclidinyl)-2H-1,4-benzoxazine-8-carboxamide hydrochloride, melting at 260°–261° C.

EXAMPLE 30

(1) A mixture of 8.6 g of 6-chloro-3,4-dihydro-4-methyl-7-nitro-3-oxo-2H-1,4-benzoxazine-8-carboxylic acid and 20 ml of thionyl chloride is refluxed under heating for 1.5 hours. After completion of the reaction, the excess thionyl chloride is distilled off under reduced pressure and further 50 ml of toluene is added thereto followed by complete removal of thionyl chloride by distillation under reduced pressure. A solution of the residue in 50 ml of methylene chloride is added dropwise to a solution of 4.1 g of 3-aminoquinuclidine and 3.6 g of triethylamine in 100 ml of methylene chloride under ice-cooling and stirring. The resultant mixture is stirred at room temperature for 4 hours followed by addition of water thereto. The crystalline insoluble substance is collected by filtration, washed with water and then dried. The crystals are recrystallized from ethanol and treated with ethanolic hydrochloric acid to give 6-chloro-3,4-dihydro-4 -methyl-7-nitro-3-oxo-N-(3-quinuclidinyl)-2H-1,4-benzoxazine-8-carboxamide hydrochloride hemihydrate, melting above 310° C. $^1$-NMR(DMSO):$\delta$(ppm)=1.50–2.32 and 2.80–4.40 (each m), 3.34 (s,3H), 4.94 (s,2H), 7.56 (s,1H), 9.52 (d,1H), 10.52 (s,1H)

(2) A solution of 10.5 g of 6-chloro-3,4-dihydro-4-methyl-3-oxo-N-(3-quinuclidinyl)-2H-1,4-benzoxazine-8-carboxamide in 50 ml of concentrated sulfuric acid is cooled to a temperature below 0° C., and a mixture of 1.5 ml of fuming nitric acid (d 1.50) and 1.5 ml of concentrated sulfuric acid is added dropwise thereto at a temperature below 5° C. The resultant mixture is stirred under ice-cooling for 1.5 hours and poured into ice-cold water. After extracting with ethyl acetate, the extract is washed with water and dried over magnesium sulfate. The solvent is distilled off followed by recrystallizing from ethanol and treating with ethanolic hydrochloric acid to give 6-chloro-3,4-dihydro-4-methyl-7-nitro-3-oxo-N-(quinuclidinyl)-2H-1,4-benzoxazine-8-carboxamide hydrochloride hemihydrate. The melting point and NMR spectra are identical with those of the compound as prepared in Example 30(1).

EXAMPLE 31

To a solution of 12 ml of 0.78N aqueous ammonium chloride and 5 ml of dimethylformamide with heating at 85° C. is added 4.8 g of powdery iron under stirring and then a solution of 8.0 g of 6-chloro-3,4-dihydro-4-methyl-7-nitro-3-oxo-N-(3-quinuclidinyl)-2H-1,4-benzoxazine-8-carboxamide in 40 ml of dimethylformamide is added over 10 minutes. The mixture is stirred at 80°–90° C. for an hour and filtered with suction through cellite under heating. The solvent is distilled off and to the residue is added 10 ml of cold water. The crystals are collected by filtration and washed with cold water and recrystallized from ethanol-water to give 7-amino-6-chloro-3,4-dihydro-4-methyl-3-oxo-N-(3-quinuclidinyl)-2H-1,4-benzoxazine-8-carboxamide hydrochloride, melting above 320° C. $^1$-NMR(DMSO):$\delta$(ppm)=1.40–2.30 and 2.76–4.50(each m), 3.22(s, 3H), 4.70(s,2H), 5.28(s,2H), 7.18(s,1H), 8.74(d,1H)

EXAMPLE 32

To a solution of 7.3 g of 7-amino-6-chloro-3,4-dihydro-4-methyl-3-oxo-N-[3-quinuclidinyl)-2H-1,3-benzoxazine-8-carboxamide in 20 ml of 35% sulfuric acid under a temperature below 15° C. is added 20 g of ice. To the mixture is added a solution of 1.76 g of sodium nitrite in 20 ml of cold water dropwise under stirring at a temperature below 5° C., and the mixture stirred at the same temperature for 5 minutes. After the excess sodium nitrite is decomposed by the addition of a small amount of urea, the solution of diazonium salt is carefully added to a solution of 4.4 g of cuprous chloride in 40 ml of concentrated hydrochloric acid. The resultant mixture is warmed for 5 minutes on a water bath. The precipitated crystals are collected by filtration, dissolved into 100 ml of water and then made alkaline with sodium hydroxide. After extracting with chloroform, the extract is washed with water and dried over magnesium sulfate. The solvent is distilled off followed by recrystallizing the residue from ethanol to give 6,7-dichloro-3,4-dihydro-4-methyl-3-oxo-N-(3-quinuclidinyl)-2H-1,4-benzoxazine-8-carboxamide, melting at 290° C. with decomposition.

EXAMPLE 33

To a solution of 45.7 g of 3-aminoquinuclidine and 38.5 g of N-methylmorpholine in 915 ml of chloroform is added portionwise 103 g of 3,4-dihydro-4-methyl-6-nitro-3-oxo-2H-1,4-benzoxazine-8-carboxylic acid chloride under stirring with ice-cooling, and the system washed with 100 ml of chloroform. The mixture is stirred at room temperature for about 1.5 hours, and allowed to stand overnight. To the resultant solution are added 1 l of water and 70 g of potassium carbonate and insoluble substances are filtered off. The chloroform layer is separated, washed with water twice and dried over magnesium sulfate. After the chloroform is distilled off, the residue is heated and dissolved into about 1.4 l of isopropyl alcohol and filtered by adding activated charcool. The filtrate is concentrated under reduced pressure and cooled. The precipitated crystals are collected by filtration, washed with isopropyl alcohol and dried. The product is purified with column chromatography using a mixed eluent of chloroform and methanol (10:1) and recrystallized from isopropyl alcohol and then ethanol. The crystals obtained are dissolved into ethanol, acidified with ethanolic hydrochloric acid and collected by filtration followed by recrystallization from methanol to give 3,4-dihydro-4-methyl-6-nitro-3-oxo-N-(3-quiniclidinyl)-2H-1,4-benzoxazine-8-carboxamide hydrochloride, melting at 306°-307° C. with decomposition.

EXAMPLE 34

To a solution of 14.2 of 3,4-dihydro-4-methyl-6-nitro-3-oxo-N-(3-quinuclidinyl)-2H-1,4-benzoxazine-8-carboxamide in 250 ml of ethanol is added Raney nickel and the mixture stirred with heating at 80°-90° C. with charging 60 atm of hydrogen gas in an autoclave. The reaction mixture is cooled and the catalyst is removed, and then the ethanol is distilled of under reduced pressure. To a solution of the residue in ethanol is added activated charcoal and the mixture filtered. The filtrate is acidified with ethanolic hydrochloric acid. The precipitated crystals are collected by filtration and recrystallized from ethanol to give 6-amino-3,4-dihydro-4-methyl-3-oxo-N-(3-quinuclidinyl)-2H-1,4-benzoxazine-8-carboxamide dihydrochloride hemihydrate, melting at 270°-271° C. with decomposition.

EXAMPLE 35

To a solution of 11.3 g of 6-amino-3,4-dihydro-4-methyl-3-oxo-N-(3-quiniclidinyl)-2H-1,4-benzoxazine-8-carboxamide in 34.2 ml of 35% sulfuric acid is added 342 ml of ice-cold water, and the solution stirred under ice-cooling. To the solution are added a solution of 3.0 g of sodium nitrite in 34 ml of water at 2°-4° C. and then a slight amount of urea followed by stirring at a temperature below 4° C. for an hour. The resultant solution is added at a temperature below 10° C. for 5 minutes dropwise to a solution of 128 g of cupric nitrate trihydrate in 1194 ml of water to which 9 g of cuprous oxide under ice-cooling is added, and then the system stirred at room temperature for an hour. The resultant mixture is adjusted to a pH of about 10 with 48% aqueous sodium hydroxide and 800 ml of chloroform is added thereto. The solution is stirred and filtered through celite. The chloroform layer is separated, washed with water and dried. After the chloroform is distilled off, the residue is purified with column chromatography using a mixed eluent of chloroform and meethanol (10:1) and recrystallized from isopropyl alcohol to give 3,4-dihydro-6-hydroxy-4-methyl-3-oxo-N-(3-quinuclidinyl)-2H-1,4-benzoxazine-8-carboxamide, melting at 250°-251° C.

EXAMPLE 36

A solution of 6 g of 6-chloro-3,4-dihydro-4-methyl-3-oxo-N-(3-quinuclidinyl)-2H-1,4-benzoxazine-8-carboxamide and 2.7 g of D-(—)-tartaric acid in 100 ml of methanol and 200 ml of ethanol is allowed to stand. The precipitated crystals are collected by filtration and re-crystallized from methanol repeatedly to give the R—(+) isomer, $[\alpha]_D^{25} = +36.72$ (c=1, chloroform), melting at 177°-178° C. This optical isomer is acidified with ethanolic hydrochloric acid, and then the precipitated crystals are collected by filtration and dried to give the R—(+) isomer hydrochloride, $[\alpha]_D^{25} = +1.4$ (c=1, water), melting at 309°-310° C. with decomposition.

By using L-(+)-tartaric acid in a similar manner, the R-(—) optical isomer, $[\alpha]_D^{25.5} = -36.76$ (c=1, chloroform), melting at 176°-178° C. is prepared. The corresponding hydrochloride, $[\alpha]_D^{25.5} = -1.2$ (c=1, water), melts at 310°-312° C. with decomposition.

EXAMPLE 37

To a solution of 5.0 g of 6-chloro-3,4-dihydro-2,4-dimethyl-3-oxo-N-(3-quinuclidinyl)-2H-1,4-benzoxazine-8-carboxamide in 150 ml of chloroform is added portionwise 3.7 g of metachloroperbenzoic acid under cooling and stirring. After 0.5 hour, ammonia gas is bubbled through the reaction solution under stirring and the precipitate is filtered off. The mother liquor is distilled off under reduced pressure followed by recrystallizing the residue from ethanol-isopropyl ester to give 6-chloro-3,4-dihydro-2,4-dimethyl-3-oxo-N-(3-quinuclidinyl)-2H-1,4-benzoxazine-8-carboxamide N-oxide, melting at 188°-190° C. with decomposition.

EXAMPLE 38

To a solution of 5.0 g of 6-chloro-3,4-dihyro-4-methyl-3-oxo-N-(3-quinuclidinyl)-2H-1,4-benzoxazine-8-carboxamide in 100 ml of chloroform with cooling at —30° C. is added 4.02 g of 80% metachloroperbenzoic acid, and the system stirred at —20° C. to —25° C. for about 30 minutes. The resultant solution is stirred at room temperature for 20 minutes and ammonia gas is bubbled into the solution at 10°-18° C. The precipitated crystals are filtered off and the filtrate is concentrated under reduced pressure. The residue is purified with column chromatography with a mixed eluent of chloroform and methanol (10:1) and to the residue is added acetonictile. The crystals are collected by filtration and recrystallized form acetonitrile to give 6-chloro-3,4-dihydro-4-methyl-3-oxo-N-(3-quinuclidinyl)-2H-1,4-benzoxazine-8-carboxamide N-oxide hemihydrate, melting at 198°-200° C. with decomposition.

EXAMPLE 39

To a solution of 4.8 g of 6-chloro-3,4-dihydro-3-oxo-N-(3-quinuclidinyl)-2H-1,4-benzoxazine-8-carboxamide in 150 ml of chloroform is added portionwise 3.7 g of metachloroperbenzoic acid under cooling and stirring. After 0.5 hour, ammonia gas is bubbled through the reaction solution under stirring and the precipitate is filtered off. The mother liquor is distilled off under reduced pressure followed by recrystallizing the residue from ethanol-isopropyl ether to give 6-chloro-3,4-dihydro-3-oxo-N-(3-quinuclidinyl)-2H-1,4-benzoxazine-8-carboxamide N-oxide.

EXAMPLE 40

To a solution of 2.6 g of 6-chloro-2-ethyl-3,4-dihydro-4-methyl-3-oxo-N-(3-quinuclidinyl)-2H-1,4-benzoxazine-8-carboxamide in 100 ml of chloroform is added portionwise 1.9 g of metachloroperbenzoic acid under cooling and stirring. After 0.5 hour, ammonia gas is bubbled through the reaction solution under stirring and the precipitate is filtered off. The mother liquor is distilled off under reduced pressure followed by recrystallizing the residue from ethanol-isopropyl ether to give 6-chloro-2-ethyl-3,4-dihydro-4-methyl-3-oxo-N-(3- quinuclidinyl)-2H-1,4- benzoxazine-8-carboxamide N-oxide.

EXAMPLE 41

To a solution of 2.7 g of N-(1-benzyl-4-piperidyl)-6-chloro-3,4-dihydro-2,4-dimethyl-3-oxo-2H-1,4-benzoxazine-8-carboxamide in 150 ml of chloroform is added portionwise 2.7 g of metachloroperbenzoic acid under cooling and stirring. After 0.5 hour, ammonia gas is bubbled through the reaction solution under stirring and the precipitate is filtered off. The mother liquor is distilled off under reduced pressure followed by recrystallizing the residue from ethanolisopropyl ether to give N-(1-benzyl-4-piperidyl)-6-chloro-3,4-dihydro-2,4-dimethyl-3-oxo-2H-1,4-benzoxazine-8-carboxamide N-oxide.

EXAMPLE 42

By using of 4-benzyl-6-chloro-3,4-dihydro-2-methyl-3-oxo-N-(3-quinuclidinyl)-2H-1,4-benzoxazine-8-carboxamide in place of 6-chloro-3,4-dihydro-2,4-dimethyl-3-oxo-N-(3-quinuclidinyl)-2H-1,4-benzoxazine-8-carboxamide, the reaction is carried out in a similar manner as described in Example 37 to give 4-benzyl-6-chloro-3,4-dihydro-2-methyl-3-oxo-N-(3-quinuclidinyl)-2H-1,4-benzoxazine-8-carboxamide N-oxide.

The following compounds are also prepared in a similar manner as mentioned above: 3,4-Dihydro-6-methoxy-4-methyl-3-oxo-N-(3-quinuclidinyl)-2H-1,4-benzoxazine-8-carboxamide; 6-Chloro-3,4-dihydro-7-hydroxy-4-methyl-3-oxo-N-(3-quinuclidinyl)-2H-1,4-benzoxazine-8-carboxamide; 6-Chloro-3,4-dihydro-7-methoxy-4-methyl-3-oxo-N-(3-quinuclidinyl)-2H-1,4-benzoxazine-8-carboxamide; 5-Amino-6-chloro-3,4-dihydro-4-methyl-3-oxo-N-(3-quinuclidinyl)-2H-1,4-benzoxazine-8-carboxamide; 5-Amino-6-chloro-3,4-dihydro-2,2,4-trimethyl-3-oxo-N-(3-quinuclidinyl)-2H-1,4-benzoxazine-8-carboxamide; 5-Acetylamino-6-chloro-3,4-dihydro-4-methyl-3-oxo-N-(3-quinuclidinyl)-2H-1,4-benzoxazine-8-carboxamide; 5-Acetylamino-6-chloro-3,4-dihydro-3-oxo-N-(3-quinuclidinyl)-2H-1,4-benzoxazine-8-carboxamide; 6-Acetylamino-3,4-dihydro-4-methyl-3-oxo-N-(3-quinuclidinyl)-2H-1,4-benzoxazine-8-carboxamide; 6-Chloro-3,4-dihydro-4-methyl-5-methylamino-3-oxo-N-(3-quinuclidinyl)-2H-1,4-benzoxazine-8-carboxamide; 3,4-Dihydro-4-methyl-5-dimethylamino-3-oxo-N-(3-quinuclidinyl)-2H-1,4-benzoxazine-8-carboxamide; 6-Chloro-4-(4-chlorobenzyl)-3,4-dihydro-2-methyl-3-oxo-N-(3-quinuclidinyl)-2H-1,4-benzoxazine-8-carboxamide; 6-Chloro-3,4-dihydro-4-[3-(4-methoxyphenyl)propyl]-3-oxo-N-(3-quinuclidinyl)-2H-1,4-benzoxazine-8-carboxamide; 6-Chloro-3,4-dihydro-2,2,4-trimethyl-3-oxo-N-(3 -quinuclidinyl)-2H-1,4-benzoxazine-8-carboxamide; 6-Fluoro-3,4-dihydro-2,4-dimethyl-3-oxo-N-(3-quinuclidinyl)-2H-1,4-benzoxazine-8-carboxamide; 3-Quinuclidinyl-6-chloro-3,4-dihydro-2,4-dimethyl-3-oxo-2H-1,4-benzoxazine-8-carboxylate; 8-Methyl-8-azabicyclo[3.2.1]oct-3-yl-6-chloro-3,4-dihydro-2,4-dimethyl-3-oxo-2H-1,4-benzoxazine-8-carboxylate; 3,4-Dihydro-N-[1-(4-methylbenzyl)-4-piperidyl]-3-oxo-2H-1,4-benzoxazine-8-carboxamide; 3,4-Dihydro-N-[1-(3,4,5-trimethoxybenzyl)-4-piperidyl]-3-oxo-2H-1,4-benzoxazepine-8-carboxamide; 5,6-Dichloro-3,4-dihydro-2,4-dimethyl-3-oxo-N-(3-quinuclidinyl)-2H-1,4-benzoxazine-8-carboxamide; 6-Chloro-3,4-dihydro-7-methoxy-2,4-dimethyl-3-oxo-N-(3-quinuclidinyl)-2H-1,4-benzoxazine-8-carboxamide; 6-Chloro-3,4-dihydro-N-{1-[1-methyl-2-(3-trifluoromethylphenyl)ethyl]-4-piperidyl}-2,4-dimethyl-3-oxo-2H-1,4-benzoxazepine-8-carboxamide; 4-(4-Carboxybenzyl) -6-chloro-3,4-dihydro-2-methyl-3-oxo-N-(3-quinuclidinyl)-2H-1,4-benzoxazine-8-carboxamide; 6-Chloro-N-{1-[3-(4-ethoxycarbonylphenoxy)propyl]-4-piperidyl}-3,4-dihydro-2,4-dimethyl-3-oxo-2H-1,4-benzoxazine-8-carboxamide; 9-Methyl-9-azabicyclo[3.3.1]non-3-yl 6-chloro-3,4-dihydro-2,4-dimethyl-3-oxo-2H-1,4-benzoxazine-8-carboxylate; 6-Chloro-3,4-dihydro-N-[1-(4-nitrobenzyl)-4-piperidyl]-3-oxo-2H-1,4-benzoxazine-8-carboxamide; N-[1-(4-Aminobenzyl)-4-piperidyl]-6-chloro-2,4-dimethyl-3-oxo-2H-1,4-benzoxazine-8-carboxamide or N-oxide thereof.

The present invention has been fully explained in the description and examples given above, but any variations and modifications thereof may be made without departing from the spirit and scope of the present invention.

We claim:

1. A benzoxazine compound of the formula:

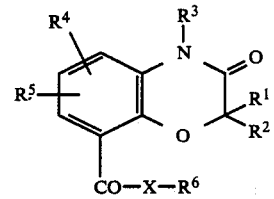

wherein $R^1$ and $R^2$ are the same or different, and each represents hydrogen or alkyl: $R^3$ represents hydrogen, alkyl, phenylalkyl or substituted phenylalkyl; $R^4$ and $R^5$ are the same or different, and each represents hydrogen, halogen, alkyl, alkoxy, amino, acylamino, alkylamino, hydroxy or nitro; X represents oxygen or NH; $R^6$ represents a group of the formula:

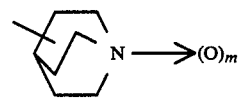

wherein m is 0 or 1, a group of the formula;

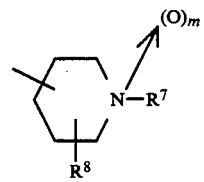

wherein $R^7$ represents alkyl, phenylalkyl, phenoxyalkyl, substituted phenylalkyl or substituted phenoxyalkyl, $R^8$ represents hydrogen or alkoxy and m is as defined above, or a group of the formula:

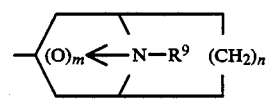

wherein $R^9$ represents alkyl, phenylalkyl or substituted phenylalkyl, n is 0 or 1, and m is as defined above, an optical isomer thereof or a pharmaceutically acceptable salt thereof.

2. The compound of claim 1, wherein X represents NH.

3. The compound of claim 1, wherein $R^4$ represents chloro or bromo at the 6-position, X represents NH and $R^6$ represents quinuclidinyl.

4. The compound of claim 1, wherein said compound is selected from the group consisting of 6-chloro-3,4-dihydro-2-methyl-3-oxo-N-(3-quinuclidinyl)-2H-1,4-benzoxazine-8-carboxamide, 6-chloro-3,4-dihydro-2,4-dimethyl-3-oxo-N-(3-quinuclidinyl)-2H-benzoxazine-8-carboxamide, 6-chloro-3,4-dihydro-N-(8-methyl-8-azabicyclo-[3.2.1]oct-3-yl)-2,4-dimethyl-3-oxo-2H-1,4-benzoxazine-8-carboxamide, 6-chloro-2-ethyl-3,4-dihydro-4-methyl-3-oxo-N-(3-quinuclidinyl)-2H-1,4-benzoxazine-8-carboxamide, 6-chloro-3,4-dihydro-4-methyl-3-oxo-N-(3-quinuclidinyl)-2H-1,4-benzoxazine-8-carboxamide, 6-bromo-3,4-dihydro-2,4-dimethyl-3-oxo-N-(3-quinuclidinyl)-2H-1,4-benzoxazine-8-carboxamide and -chloro-3,4-dihydro-2,2,4-trimethyl-3-oxo-N-(3-quinuclidinyl)-2H-1,4-benzoxazine-8-carboxamide, optical isomers thereof, and pharmaceuticaly acceptable acid addition salts thereof.

5. A pharmaceutical composition comprising the compound of claim 1 and a pharmaceutically acceptable additive.

* * * * *